United States Patent [19]

Stacy

[11] Patent Number: 4,728,344
[45] Date of Patent: Mar. 1, 1988

[54] POLYMER ANALYSIS

[75] Inventor: Carl J. Stacy, Bartlesville, Okla.

[73] Assignee: Phillips Petroleum Company, Bartlesville, Okla.

[21] Appl. No.: 634,924

[22] Filed: Jul. 26, 1984

[51] Int. Cl.$^4$ .............................................. B01D 15/08
[52] U.S. Cl. .......................................... 55/67; 73/23.1
[58] Field of Search .......................... 55/197, 386, 67; 73/23.1, 61.1 C, 863.11, 864.83; 210/198.2, 198.3; 422/70, 81

[56] References Cited

U.S. PATENT DOCUMENTS

| | | | |
|---|---|---|---|
| 3,225,520 | 12/1965 | Burow | 73/23.1 X |
| 3,225,521 | 12/1965 | Burow | 73/23.1 X |
| 3,385,099 | 5/1968 | Diem et al. | 73/23.1 |
| 3,403,545 | 10/1968 | Carter | 73/23.1 |
| 3,458,437 | 7/1969 | Ouano | 55/386 X |
| 3,522,725 | 8/1970 | Waters | 73/61.1 C |
| 3,592,046 | 7/1971 | Cramers | 73/23.1 |
| 3,719,084 | 3/1973 | Walker | 73/23.1 |
| 3,910,765 | 10/1975 | Tinklepaugh et al. | 73/23.1 X |
| 4,035,168 | 7/1977 | Jennings | 73/23.1 X |
| 4,044,593 | 8/1977 | Haruki et al. | 73/23.1 |
| 4,133,640 | 1/1979 | Clinton et al. | 73/23.1 X |
| 4,181,613 | 1/1980 | Welsh et al. | 73/23.1 X |
| 4,204,423 | 5/1980 | Jordan | 73/61.1 C X |
| 4,258,564 | 3/1981 | Hulme et al. | 73/61.1 C |
| 4,271,703 | 6/1981 | Roof | 73/863.11 |
| 4,294,799 | 10/1981 | Stephens et al. | 422/70 X |
| 4,420,679 | 12/1983 | Howe | 73/23.1 X |

OTHER PUBLICATIONS

Ouano, "Gel-Permeation Chromotography. VIII. Molecular Weight Detection of GPC Effluents", J. of Polymer Sc.: Part A-1, vol. 10, 2169-2180 (1972).
Kraus et al., "Molecular Weight and . . . Solution Viscometry", J. of Polymer Sc.: Part A-2, vol. 10, 657-672 (1972).
"Universal Calibration of Polymer Material", pp. 509-518, 1979.

*Primary Examiner*—Robert Spitzer
*Attorney, Agent, or Firm*—Williams, Phillips & Umphlett

[57] ABSTRACT

In the analysis of polymers which are generally soluble only at elevated temperatures, at least the chromatographic columns in a high pressure liquid chromatography system for the analysis of such polymers are located in an oven maintained at a temperature suitable for maintaining the polymer in solution. Preferably, the detector used is also operable at such elevated temperatures. However, other apparatus such as pumps and injectors are operated at lower temperatures.

6 Claims, 5 Drawing Figures

POLYMER ANALYSIS

This invention relates to the analysis of polymers. In one aspect, this invention relates to the analysis of polymers which are soluble only at elevated temperatures.

The application of high-pressure liquid chromatography techniques, such as size exclusion chromatography and gel permeation chromatography, to polymers which are soluble only at elevated temperatures is restricted by problems in developing pumps, injectors, detectors, and other auxiliary units which are operable at elevated temperatures. As an example, certain arylene sulfide polymers, such as polyphenylene sulfide, are soluble only above 200° C. which is significantly above the temperature at which commercial, high-pressure liquid chromatography systems are designed to operate. Commercial systems will generally not operate above 150° C.

It is thus an object of this invention to provide method and apparatus suitable for the analysis of polymers which can be utilized to analyze polymers which are soluble only at elevated temperatures.

In accordance with the present invention, at least the chromatographic columns in a high-pressure liquid chromatography system for the analysis of polymers are located in an oven maintained at a temperature suitable for maintaining the polymer in solution. Preferably, a detector is also used which is operable at elevated temperatures and thus may be placed in the oven. However, other apparatus such as pumps and injectors are operated outside of the oven and at lower temperatures. A heat exchanger is utilized to bring the sample to be analyzed to the desired temperature after the sample is injected into the carrier fluid but before the sample contained in the carrier fluid passes through the chromatographic columns. In this manner, the problem of developing apparatus such as pumps and injectors which are operable at high temperatures is overcome and an analysis of polymers soluble only at elevated temperatures is accomplished.

Other objects and advantages of the invention will be apparent from the foregoing brief description of the invention and the claims as well as the detailed description of the drawings which are briefly described as follows:

While the present invention is particularly applicable to the analysis of polymers which are soluble only at elevated temperatures, any suitable polymer can be analyzed in accordance with the present invention. This will be particularly illustrated in the examples where a polymer soluble at low temperatures was utilized for calibration purposes. Since commercial equipment is available which will operate at about 150° C., the invention is espcially applicable to the analysis of polymers which are soluble only above 150° C.

The invention has been particularly applied to the analysis of Ryton ® polyphenylene sulfide (soluble only above about 200° C.) and will be described in terms of such an analysis. However, again, the invention is applicable to the analysis of any suitable polymer.

Figure 1:
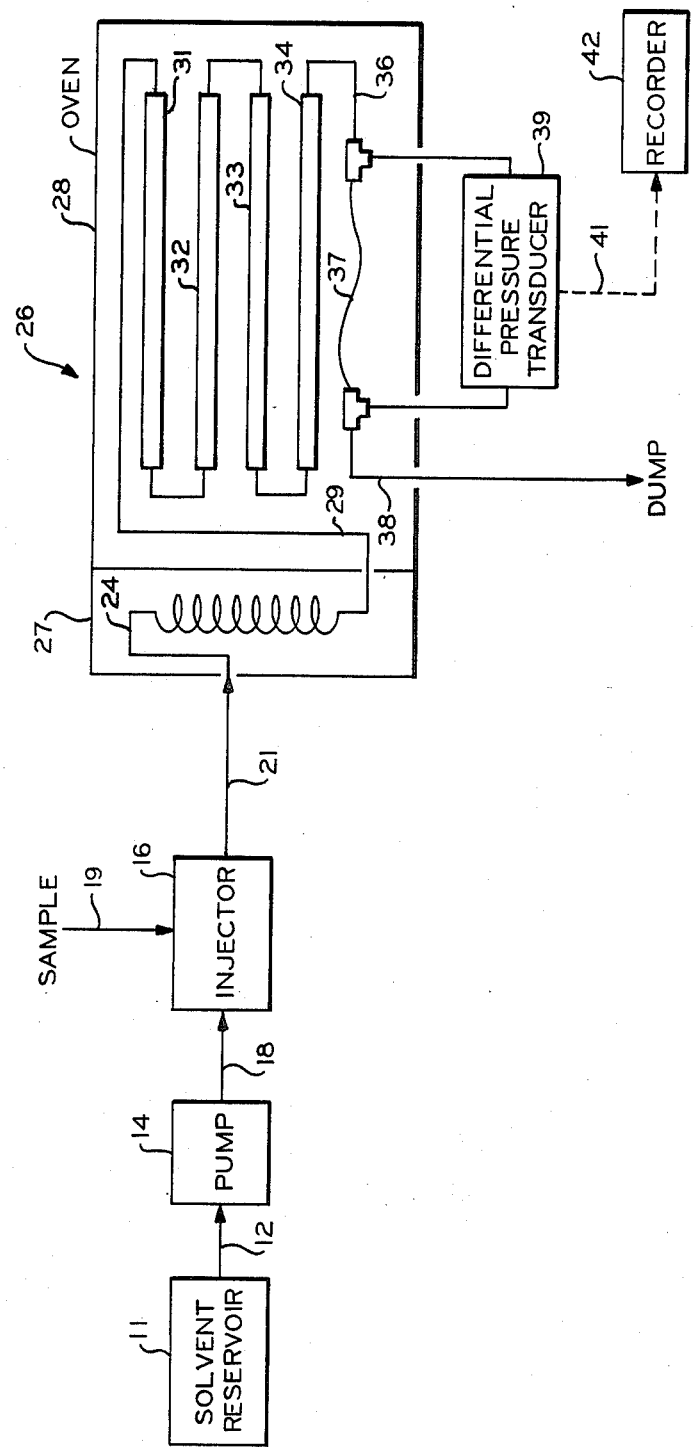
FIG. 1 is a diagrammatic illustration of the apparatus utilized in accordance with the present invention to analyze polymers.

Referring now to FIG. 1, the solvent reservoir 11 contains a solvent for the particular polymer being analyzed. The solvent is utilized as the carrier fluid.

Any suitable solvent for the polymer being analyzed may be used. For polyphenylene sulfide, suitable solvents include 1-chloronaphthalene, diphenyl ether, N-methyl-2-pyrrolidone, dibenzofuran and triethylene tetramine. Of these solvents, 1-chloronaphthalene is preferred.

The solvent contained in reservoir 11 is provided through conduit 12 to the pump 14 and then pumped through the pump 14 to the injector 16 through conduit 18. Any suitable pump may be utilized. An example of a suitable pump is a 6000A manufactured by Waters.

Any suitable injector may be utilized to inject the polymer sample provided through conduit 19 into the carrier fluid flowing through conduit 18. A suitable injector is the U6K manufactured by Waters. Also, various six port sample valves, such as those supplied by Applied Automation, Inc., may be utilized.

The sample of polymer flowing through conduit 19 is preferably processed such that the polymer is diluted in a solvent and is in the form of a suspension which can be easily handled at temperatures substantially lower than the temperature at which the polymer is soluble. For polyphenylene sulfide, this is preferably accomplished by stirring the polymer to be analyzed in a solvent for the polymer at about 220° C. until the polymer is completely dissolved. The resulting solution is then preferably filtered to remove foreign material and then cooled to the desired temperature for injection. The polyphenylene sulfide will precipitate into a finely divided form which will remain suspended in the solvent.

Any suitable solvent may be utilized to prepare the polymer sample. However, preferably the solvent used to prepare the sample is the same solvent as is used for the carrier fluid.

The sample may contain any suitable concentration of the polymer. Preferably, the concentration of the polymer is very small which increases the speed at which the polymer will return to solution upon being heated to an elevated temperature as described hereinafter. Thus, the concentration of the polymeer will preferably be in the range of about 0.05 to about 0.5 $\mu g/\mu L$.

Any suitable volume of the sample may be injected into the carrier fluid. Preferably, the volume of sample injected will be in the range of about 25 $\mu L$ to about 250 $\mu L$. The volume to be injected is generally determined by the molecular weight of the polymer. Low molecular weight polymers require larger samples for suitable sensitivity.

The pump and injector may be operated at any suitable temperature but generally such temperature will be much lower than the oven temperature. A temperature of 30° C. was used for polyphenylene sulfide.

After injection into the carrier fluid, the sample is provided from the injector 16 through conduit 21 to the preheater 24 which is located in the oven 26. The oven 26 is preferably divided into two compartments 27 and 28. Compartment 27 is preferably maintained at a higher temperature than compartment 28 to facilitate the rapid dissolving of the polymer in the heat exchanger 24. As an example, for polyphenylene sulfide, compartment 27 is preferably maintained at about 240° C. while compartment 28 is preferably maintained at about 210° C. However, any suitable temperatures could be utilized with the temperature generally being determined by the characteristics of the particular polymer being analyzed. It is also noted that separate ovens may be used for compartments 27 and 28 if desired.

Any suitable preheating arrangement may be utilized. Preferably, a coiled tube is utilized to facilitate the transfer of heat to the sample. An example of a suitable preheater is 5 feet of 0.01 inch stainless steel tubing wound on a 1 inch diameter brass rod.

Any suitable residence time may be utilized for the sample in the preheater 24. The residence time should be such that, at the temperature at which the preheater 24 is maintained, the polymer will be in solution before the polymer leaves the preheater 24. An example of a suitable residence time for polyphenylene sulfide is about 1 minute at a temperature in the range of about 230° C. to about 260° C.

From the preheater 24 the sample, which is now in solution, is provided through conduit 29 to chromatograhic column 31 which is the first of a plurality of chromatographic columns in series. From column 31 the sample flows through column 32 and then columns 33 and 34.

Any suitable number and type of chromatographic columns may be utilized which provide the desired separation of the components of the polymer being analyzed. Also, the columns must be able to withstand the temperature in the oven compartment 28 which will be determined by the characteristics of the particular polymer being analyzed. For polyphenylene sulfide, four columns in series is preferred with all of the columns being gel permeation chromatography columns manufactured by Waters. Column 31 is preferably a $\mu$-Porasil GPC 60A. Column 32 is prefersbly a $\mu$-Bondagel E 125. Column 33 is preferably a $\mu$-Bondagel E 500 and column 34 is preferably a $\mu$-Bondagel E High A.

As an example of a variation in the number of columns, for the analysis of polyphenylene sulfide only columns 31, 32, and 33 were originally used. The analysis was satisfactory but it was found that the addition of column 34 improved the resolution of high molecular weight species as will be illustrated more fully in the Examples.

The columns 31-34 act to separate the polymer sample into its components. Larger molecules will be eluted first.

As the sample is eluted from column 34, the sample is provided through conduit 36 to a detector which is made up of capillary tubing 37 and a differential pressure transducer 39. The sample passes through the capillary tubing 37 and then is dumped through conduit 38.

Any suitable size and length of capillary tubing may be utilized for the capillary tubing 37. For polyphenylene sulfide, suitable capillary tubing consists of 7 inches of 0.01 inch capillary tubing.

The portion of conduit 38 immediately following the capillary tubing 37 preferably has a small diameter to provide some outlet pressure drop. Again, for polyphenylene sulfide, a 10 inch section of 0.01 inch stainless steel tubing was utilized and then finally a 5 inch section of 0.04 inch stainless steel tubing was utilized to exit the oven. The larger diameter is preferred at the exit to prevent clogging at the cooler end of conduit 38.

The differential pressure transducer 39 provides an output signal 41 which is representative of the differential pressure across the capillary tubing 37. Signal 41 is provided from the differential pressure transducer to the recorder 42 which records the output from the differential pressure transducer 39 at all times during the analysis.

As will be discussed more fully hereinafter, higher concentrations of a particular component of the polymer will result in higher differential pressure drops across the capillary tube 37. However, larger molecules also result in higher pressure drops than smaller molecules. It is thus necessary to calibrate the output from the differential pressure transducer 41 to compensate for the fact that the same concentration of a larger molecule will result in a higher differential pressure drop across the capillary tube 37 than the same concentration of smaller molecules.

It is noted that other suitable detectors may be utilized if desired. An example of another suitable detector is a light scattering detector located outside the oven. However, such a detector was found to be susceptible to clouding of the optical windows by precipitate. Thus the preference for a detector which may be operated at elevated temperatures.

In operation, it is first necessary to calibrate the apparatus illustrated in FIG. 1. If good standards (known molecular weight and narrow molecular weight distribution) for the particular polymer being analyzed are available, then calibration is accomplished by individually injecting such known standards and noting the time at which a peak differential pressure is measured. Since the molecular weight of the standards would be known, a correlation could be obtained between molecular weight and the time that the particular molecular weight produced a peak differential pressure. Such correlation can be utilized to determine the molecular weight of various components in an unknown sample of the same polymer.

Once the molecular weight to time calibration has been made, the relative concentration ($C_R$) of a particular component (i) in the polymer may be determined as follows.

Figure 2:
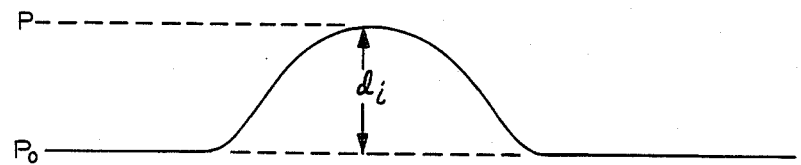
FIG. 2 is an illustration of the deflection of a recording instrument as a polymer is analyzed.

Referring now to FIG. 2, assume that the base line differential pressure is given by $P_o$. Also assume that, for component (i), the measured differential pressure is P and the deflection of the recording instrument is given by $d_i$.

It is known that viscosity $[\eta]$ of component (i) is given by $$[\eta]_i = KM_i^a \qquad (1)$$

where $[\eta]_i$ = viscosity of component (i);
M = molecular weight of component (i); and
K and a are constants.

It is also known that the viscosity of component (i), at low concentrations of component (i), is given by $$[\eta]_i = \frac{kd_i}{P_o C_{Ai}} \qquad (2)$$

where $C_{Ai}$ is the absolute concentration of component (i), k is a constant and $[\eta]_i$, $d_i$ and $P_o$ are as previously defined.

Combining equations (1) and (2) and rerranging gives $$C_{Ai} = \frac{kd_i}{P_o K M_i^a} \qquad (3)$$

Thus, the relative concentration of component (i) is given by $$C_{Ri} = \frac{\frac{kd_i}{P_0 K M_i}}{\frac{k}{P_0 K} \sum_{i=1-n} \frac{d_i}{M_i^a}} \quad \frac{\frac{d_i}{M_i}}{\sum_{i=1-n} \frac{d_i}{M_i^a}} \quad (4)$$

where n is the number of components and all other terms are as previously defined. Thus, the relative concentration of any component contained in a sample may be determined in accordance with equation (4) by running the entire sample through the apparatus illustrated in FIG. 1, noting the deflection for each component and then utilizing equation (4) to calculate the relative concentration of each component.

For polyphenylene sulfide, good standards were not available and this may often be the case in the analysis of polymers. Under such circumstances, a universal calibration such as disclosed by Lloyd R. Snyder in "Introduction to Modern Liquid Chromatography, John Wiley & Sons, Inc., 1979 may be utilized. From the universal calibration theory, it is known that the hydrodynamic volum (V) of a component (i) of any polymer is given by $$V_i = K M_i^{a+1} \quad (5)$$

where the variables are as previously defined. Using this relationship in equation (4) gives $$C_{Ri} = \frac{\frac{d_i}{V_i^{\frac{a}{a+1}}}}{\sum_{i=1-n} \frac{d_i}{V_i^{\frac{a}{a+1}}}} \quad (6)$$

Figure 3:
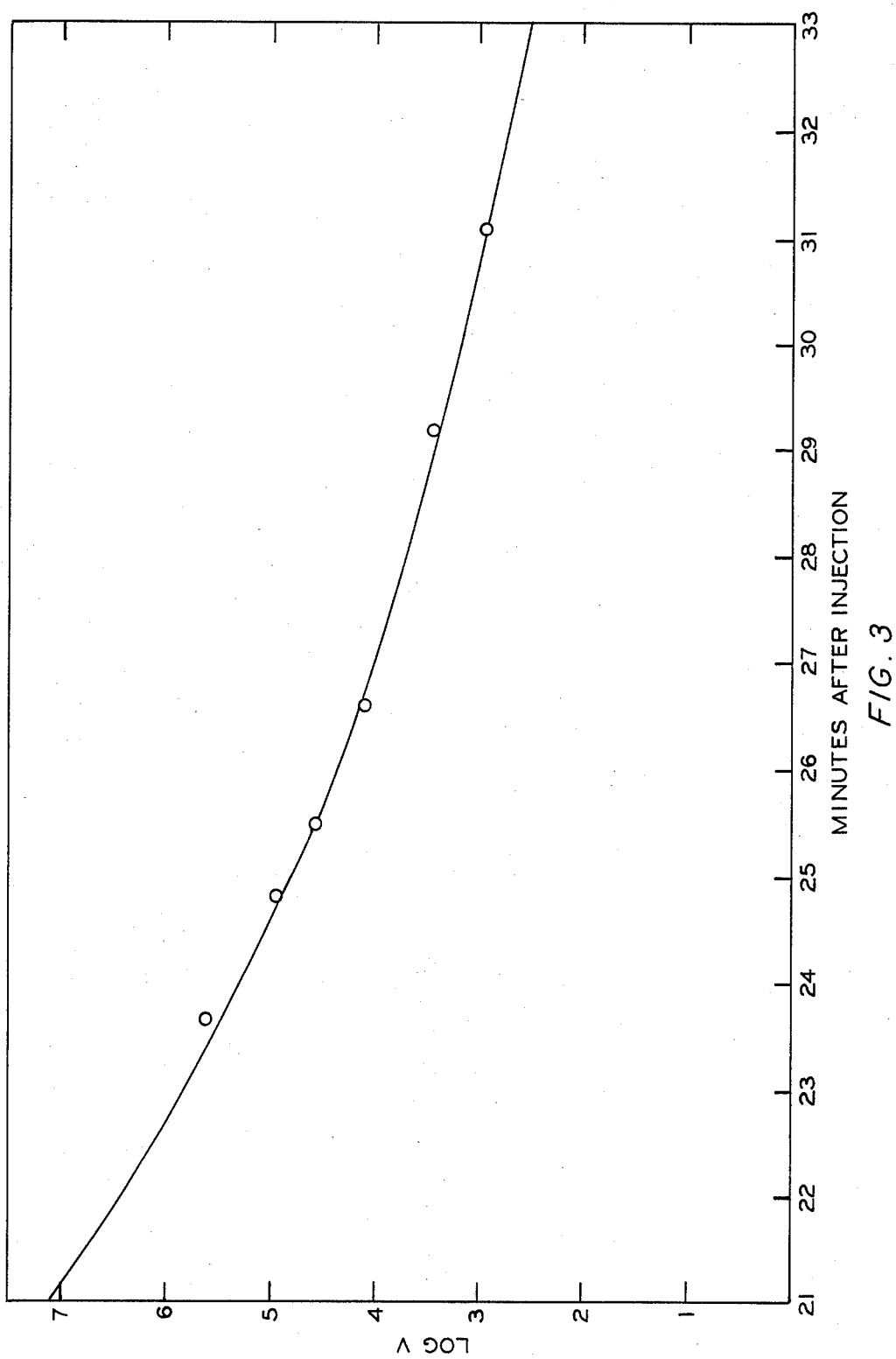
FIG. 3 is an illustration of a calibration curve.

Thus, the apparatus illustrated in FIG. 1 may be calibrated for polyphenylene sulfide by using standards having a known hydrodynamic volume and determining when peaks occur. Such a calibration, using polystyrene standards, is illustrated in FIG. 3. Once the calibration curve illustrated in FIG. 3 is obtained, the hydrodynamic volume of the component going through the detector at any particular time will be known for polyarylene sulfide even though polystyrene was used to obtain the calibration curve. As an example, at 28 minutes, the hydrodynamic volume of the component in the detector will have a logarithm of about 3.7. The hydrodynamic volumes can be utilized in equation (6) to determine the relative concentration of each component in the polymer. Further, the hydrodynamic volume can be utilized in equation (5) to determine the molecular weight of the components of the polymer.

The constants K and a were determined by actually measuring viscosity and also actually measuring molecular weight of at least two samples and then calculating K and a. For polyarylene sulfide, K was determined to be $8.91 \times 10^{-5}$ and a was determined to be 0.747.

It is noted that, while the foregoing discussion is in terms of a particular component, in actual practice concentration is measured for a particular time period and not a discreet point in time. A preferred time period is about 0.2 minutes.

The following examples are presented in further illustration of the invention.

EXAMPLE 1

A sample of polyphenylene sulfide to be analyzed was prepared by putting weighed amounts of polyphenylene sulfide and solvent (1-chloro naphthalene) into a container fitted with a valve and filter. The concentration of polyphenylene sulfide was 0.2 weight percent. The container was purged with nitrogen and then sealed. The contents of the container was then magnetically stirred at 220° C. until the polyphenylene sulfide was completely in solution. The container was then quickly inverted and the valve opened. Internal pressure was sufficient to drive the solution into a small flask which was at room temperature. A suspended precipitate of the polyphenylene sulfide formed. The particles were small enough to easily pass through 0.01 inch stainless steel tubing. 100 microliters of the suspension was then injected through the injector 16 illustrated in FIG. 1.

Results of the analysis are illustrated in Table I.

TABLE I

| Input Min. | Height | Corr. Height | Conc. (Wt. %) | Molecular Weight |
|---|---|---|---|---|
| 23 | 103 | 0 | 0.000 | 553442 |
| 23.2 | 109 | 0 | 0.000 | 469891 |
| 23.4 | 112 | 5 | 0.013 | 400647 |
| 23.6 | 113 | 9 | 0.026 | 343034 |
| 23.8 | 122 | 20 | 0.065 | 294913 |
| 24 | 141 | 41 | 0.150 | 254566 |
| 24.2 | 168 | 71 | 0.288 | 220612 |
| 24.4 | 214 | 119 | 0.536 | 191934 |
| 24.6 | 278 | 186 | 0.928 | 167623 |
| 24.8 | 353 | 263 | 1.447 | 146943 |
| 25 | 435 | 347 | 2.101 | 129291 |
| 25.2 | 514 | 429 | 2.851 | 114173 |
| 25.4 | 591 | 508 | 3.695 | 101181 |
| 25.6 | 660 | 579 | 4.597 | 89980 |
| 25.8 | 705 | 627 | 5.420 | 80294 |
| 26 | 725 | 649 | 6.093 | 71891 |
| 26.2 | 715 | 642 | 6.530 | 64578 |
| 26.4 | 673 | 602 | 6.618 | 58196 |
| 26.6 | 619 | 550 | 6.520 | 52611 |
| 26.8 | 561 | 495 | 6.313 | 47707 |
| 27 | 500 | 436 | 5.968 | 43391 |
| 27.2 | 440 | 378 | 5.542 | 39582 |
| 27.4 | 386 | 327 | 5.124 | 36211 |
| 27.6 | 340 | 283 | 4.729 | 33220 |
| 27.8 | 294 | 240 | 4.269 | 30560 |
| 28 | 251 | 199 | 3.760 | 28188 |
| 28.2 | 213 | 163 | 3.265 | 26067 |
| 28.4 | 179 | 132 | 2.798 | 24167 |
| 28.6 | 150 | 105 | 2.351 | 22461 |
| 28.8 | 129 | 86 | 2.030 | 20926 |
| 29 | 108 | 68 | 1.689 | 19540 |
| 29.2 | 87 | 49 | 1.279 | 18288 |
| 29.4 | 71 | 36 | 0.986 | 17154 |
| 29.6 | 60 | 27 | 0.774 | 16124 |
| 29.8 | 49 | 18 | 0.540 | 15187 |
| 30 | 40 | 12 | 0.376 | 14332 |
| 30.2 | 34 | 8 | 0.261 | 13552 |
| 30.4 | 26 | 2 | 0.068 | 12838 |
| 30.6 | 18 | 0 | 0.000 | 12184 |
| 30.8 | 13 | 0 | 0.000 | 11582 |
| 31 | 8 | 0 | 0.000 | 11028 |
| 31.2 | 4 | 0 | 0.000 | 10518 |
| 31.4 | 0 | 0 | 0.000 | 10046 |
| 31.6 | −5 | 0 | 0.000 | 9609 |
| 31.8 | −7 | 0 | 0.000 | 9204 |
| 32 | −9 | 0 | 0.000 | 8827 |
| 32.2 | −10 | 0 | 0.000 | 8476 |
| 32.4 | −9 | 0 | 0.000 | 8149 |
| 32.6 | −7 | 0 | 0.000 | 7843 |
| 32.8 | −5 | 0 | 0.000 | 7556 |
| 33 | −5 | 0 | 0.000 | 7286 |

The height given in Table I was the height of the recording pen which increased or decreased as the differential pressure increased or decreased. The column labeled Input Minutes is the elapsed time since injection of the sample into the carrier fluid. The column labeled Corrected Height represents the result after subtracting base line. The base line for this particular analysis was sloping. The concentration and molecular weight, as calculated in accordance with equations (5) and (6), show an increse in concentration until the maximum concentration was reached at a molecular weight of about 58,196 and then the concentration began to decrease.

EXAMPLE 2

Figure 4:
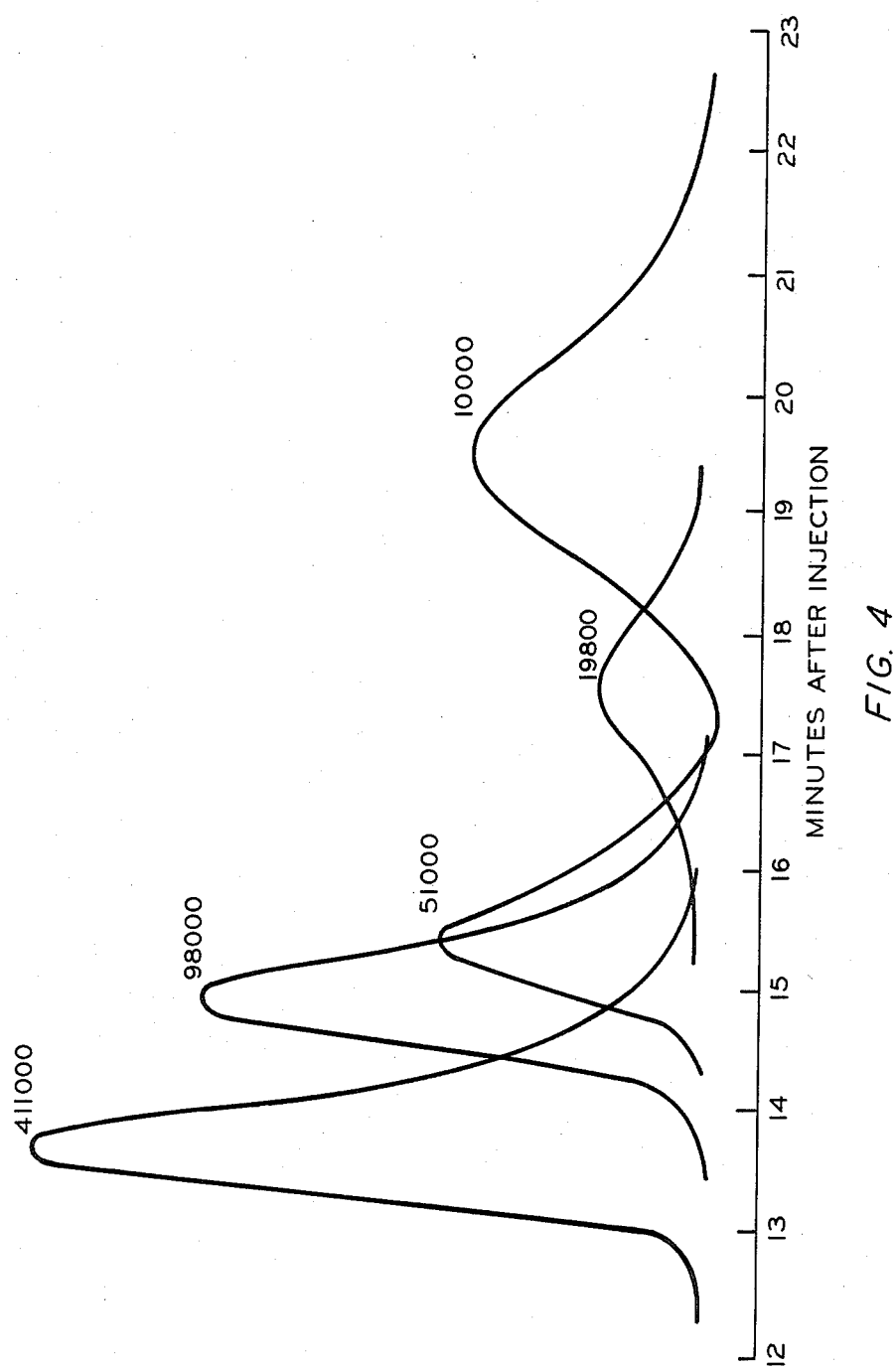
FIGS. 4 and 5 are illustrations of the analysis of polystyrene standards using three and four columns respectively.
Figure 5:
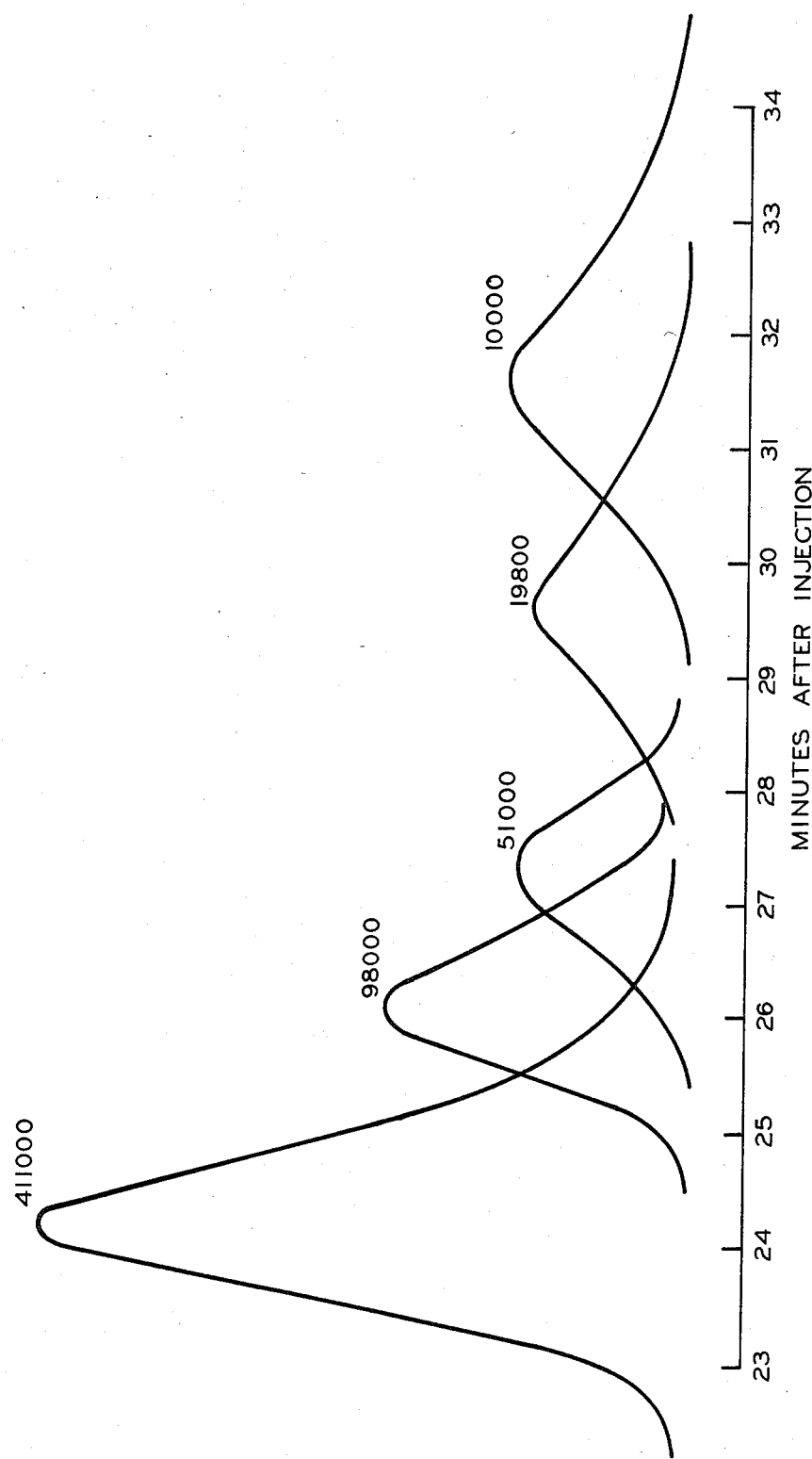

To illustrate the benefit of using the four column system illustrated in FIG. 1 as opposed to a three column system using only columns 31-33 illustrated in FIG. 1, five polystyrene standards having known molecular weight and narrow molecular weight distribution were run in both a three column and a four column system under identical conditions. The results of the three column run are illustrated in FIG. 4 while the results of the four column run are illustrated in FIG. 5. The molecular weight of the standards is also set forth in FIGS. 4 and 5.

Referring to FIGS. 4 and 5, it can be seen that better separation of the peaks is obtained by the four column system. The better separation is particularly noted for the standards having a molecular weight of 98,000 and 51,000.

Reasonable variations are possible within the scope of the foregoing disclosure and the appended claims.

That which is claimed is:

1. A method for determining the relative concentration of a component in a polymer which is soluble only above about 150° C., said method comprising the steps of:

injecting a desired volume of a sample of said polymer into a carrier fluid at a time $T_1$, wherein said injection is accomplished at a first temperature and wherein said carrier fluid is a solvent for said polymer;

heating said carrier fluid containing said sample of said polymer until said polymer is completely in solution, wherein the temperature at which said polymer is soluble in said carrier fluid (second temperature) is greater than said first temperature;

providing the heated carrier fluid containing said sample of said polymer in solution to the fluid inlet of the first one of a plurality of chromatographic columns in series to thereby provide said sample of said polymer to the fluid inlet of said first one of said plurality of chromatographic columns in series, wherein said plurality of chromatographic columns are maintained at at least said second temperature; and providing said carrier fluid from the fluid outlet of the last one of said plurality of chromatographic columns in series to the fluid inlet of a detector capable of providing an output signal which is responsive to the concentration of components of said polymer, wherein said detector provides an output signal at time $T_2$ which is responsive to the relative concentration of the component of said polymer in said detector at said time $T_2$ and wherein said time $T_2$ is later in time than said time $T_1$.

2. A method in accordance with claim 1 wherein said first temperature is about 30° C.

3. A method in accordance with claim 1 wherein said polymer is polyphenylene sulfide and wherein said carrier fluid is selected from the group consisting of 1-chloronaphthalene, diphenyl ether, N-methyl-2-pyrrolidone, dibenzofuran and triethylene tetramine.

4. A method in accordance with claim 3 wherein said second temperature is above about 200° C.

5. A method in accordance with claim 1 wherein said plurality of chromatographic columns comprises four chromatographic columns, wherein each of the four chromatographic columns is a gel permeation chromatography column and wherein each of the four gel permeation chromatography columns is sized so as to pass different size molecules at different rates with respect to the other gel permeation chromatography columns.

6. A method in accordance with claim 1 wherein said detector is maintained at at least said second temperature, wherein said detector is a suitable length of capillary tubing and wherein said output signal is a measurement of the differential pressure across said capillary tubing.

* * * * *